United States Patent [19]

Doss et al.

[11] 4,016,886
[45] Apr. 12, 1977

[54] METHOD FOR LOCALIZING HEATING IN TUMOR TISSUE

[75] Inventors: James D. Doss; Charles W. McCabe, both of Los Alamos, N. Mex.

[73] Assignee: The United States of America as represented by The United States Energy Research and Development Administration, Washington, D.C.

[22] Filed: Nov. 26, 1974

[21] Appl. No.: 527,469

[52] U.S. Cl. .............................. 128/422; 128/399; 128/404
[51] Int. Cl.² .......................................... A61N 1/32
[58] Field of Search .............. 28/1.3, 1.5, 362, 399, 28/401, 402, 404, 405, 407, 413, 418, 419, 421, 422, 423

[56] References Cited

UNITED STATES PATENTS

| 2,179,261 | 11/1939 | Keller | 128/422 |
| 2,259,318 | 10/1941 | Mouromtseff | 128/422 |

FOREIGN PATENTS OR APPLICATIONS

| 1,143,937 | 2/1963 | Germany | 128/404 |
| 699,114 | 11/1940 | Germany | 128/419 |
| 6,804,714 | 10/1968 | Netherlands | 128/418 |
| 530,528 | 12/1940 | United Kingdom | 128/413 |
| 1,045,546 | 10/1966 | United Kingdom | 128/404 |

OTHER PUBLICATIONS

Goldenberg et al., "Zeitschrift For Natureforschung", vol. 26b, Teil 8, Apr. 1971, pp. 359–361.
Geyser, "Fischer's Magazine", vol. 3, Dec. 1924, pp. 6–9.
Martin et al., "Journal of the American Medical Association, vol. 142, No. 1, pp. 27–32, Jan. 7, 1950.

Primary Examiner—William E. Kamm
Attorney, Agent, or Firm—Dean E. Carlson; Jerome B. Rockwood

[57] ABSTRACT

A method for a localized tissue heating of tumors is disclosed. Localized radio frequency current fields are produced with specific electrode configurations. Several electrode configurations are disclosed, enabling variations in electrical and thermal properties of tissues to be exploited.

2 Claims, 8 Drawing Figures

METHOD FOR LOCALIZING HEATING IN TUMOR TISSUE

BACKGROUND OF THE INVENTION

Hyperthermia, raising the temperature of tissue by the application of heat, has proven to be useful of the treatment of tumors particularly in combination with radiation therapy or chemotherapy. As a result the need has arisen for practical methods of providing localized heating in arbitrary tissue volumes. Heating superficial tumors in hot water baths has been proposed, but the method has very limited clinical application. Microwave and ultrasound diathermy are capable of greater penetration than external conduction heating, but are also generally limited to the heating of superficial tissue volumes.

In the contrast with the prior art limitation to essentially superficial tissue heating, the present invention enables localized tissue heating by electric current fields produced by specified electrode configurations of deeply embedded tumors virtually anywhere in the body. Heat may be applied in almost any treatment volumes specified by the therapist. Variations in electrical and thermal properties of tissues can be exploited to improve the treatment procedure. It is well known that different body tissues have widely varying values of resistivity and dielectric constant. The resistivity of bone and fat is so high in relation to that of well-perfused tissues that one may consider bone and fat as electrical insulators. Thus, fat may have a resistivity of 1,000 to 3,000 ohm cm, compared to 200 ohm cm for typical muscle tissue. These variations in resistivity, while sometimes troublesome in forming treatment fields in connection with the present invention, may often be used to advantage. For example, the electrical current easily flows through a well perfused tumor volume immediately adjacent to the spinal column, while making only comparatively slight penetration of the spinal cord itself. This is due to the fact that the spinal cord is surrounded by the relatively high-resistance bone structure. Thus, the tumor volume could be heated to a level sufficient for radio sensitation, i.e., 42° to 43° C while the spinal cord remains essentially unheated with normal radiation sensitivity.

SUMMARY OF THE INVENTION

The present invention comprises essentially a low frequency radio frequency generator operating in the area between 100 kHz and 1 MHz connected to a pair of electrodes which may vary in configuration and location. Temperature of the tissue to be heated is sensed by a thermistor, and the output of the radio frequency generator is amplitude modulated to attain and maintain the desired temperature. The shape and location of the heating field may be controlled by selecting a particular figuration of electrodes. The position of the electrodes may be selected to provide the desirable heat in the tumor tissue while not heating healthy tissue nearby. In addition, a monitoring device may be employed to shut off the radio frequency generator if the tissue temperature becomes too high for safety.

DESCRIPTION OF THE INVENTION

Figure 1:
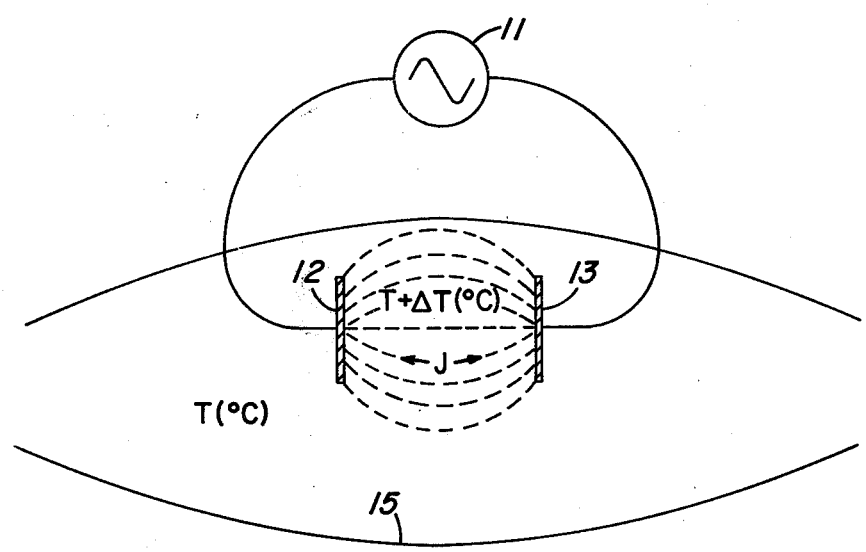
FIG. 1 schematically illustrates the basic principles of the present invention.
Figure 3:
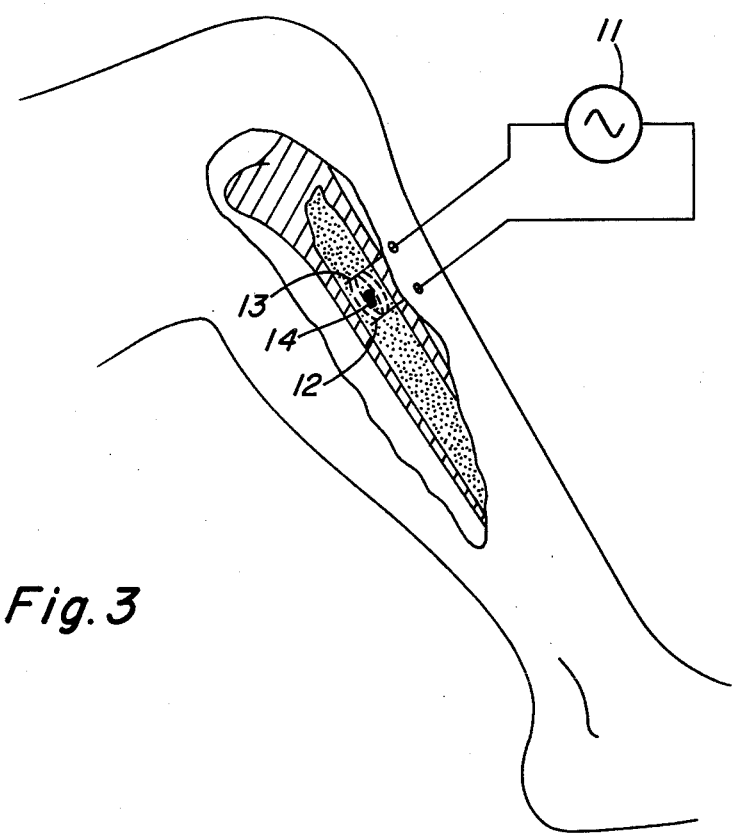
FIG. 3 illustrates application of the present invention in connection with bone structure.

The basic principle of the present invention is illustrated in FIG. 1. An alternating electrical current provided by generator 11 is applied to electrodes 12 and 13. Alternating current flows through the treatment volume between the electrodes, as indicated by the dashed lines. The effect of the electrical field J on tissue may be resolved into two components, resistive and capacitive, respectively. It is the resistive component which causes energy dissipation in the tissue. The capacitive component of the alternating current causes no energy dissipation in the tissue and therefore, does not contribute to increasing the temperature in the treatment volume. For high efficiency it is desirable to minimize the capacitive current. This may be accomplished primarily by using a relative low frequency, since the impedance to the capacitive current flow is inversely proportional to frequency. However, if the frequency employed is too low, nerve and muscle fibers may be depolarized. Therefore, radio frequency oscillator 11 is designed to provide a frequency between 100 kHz and 1 MHz as a compromise providing a suitable range of operation. Electrodes 12 and 13 are not significantly heated by the electrical current due to high electrical conductivity of the electrodes. As electrical field J passes through the tissue, the resistive component heats the tissue, causing a temperature rise therein by an increment $\Delta T$. Therefore the temperature of the tissue electrodes 12 and 13 is heated to a temperature $T + \Delta T$.

Figure 2:
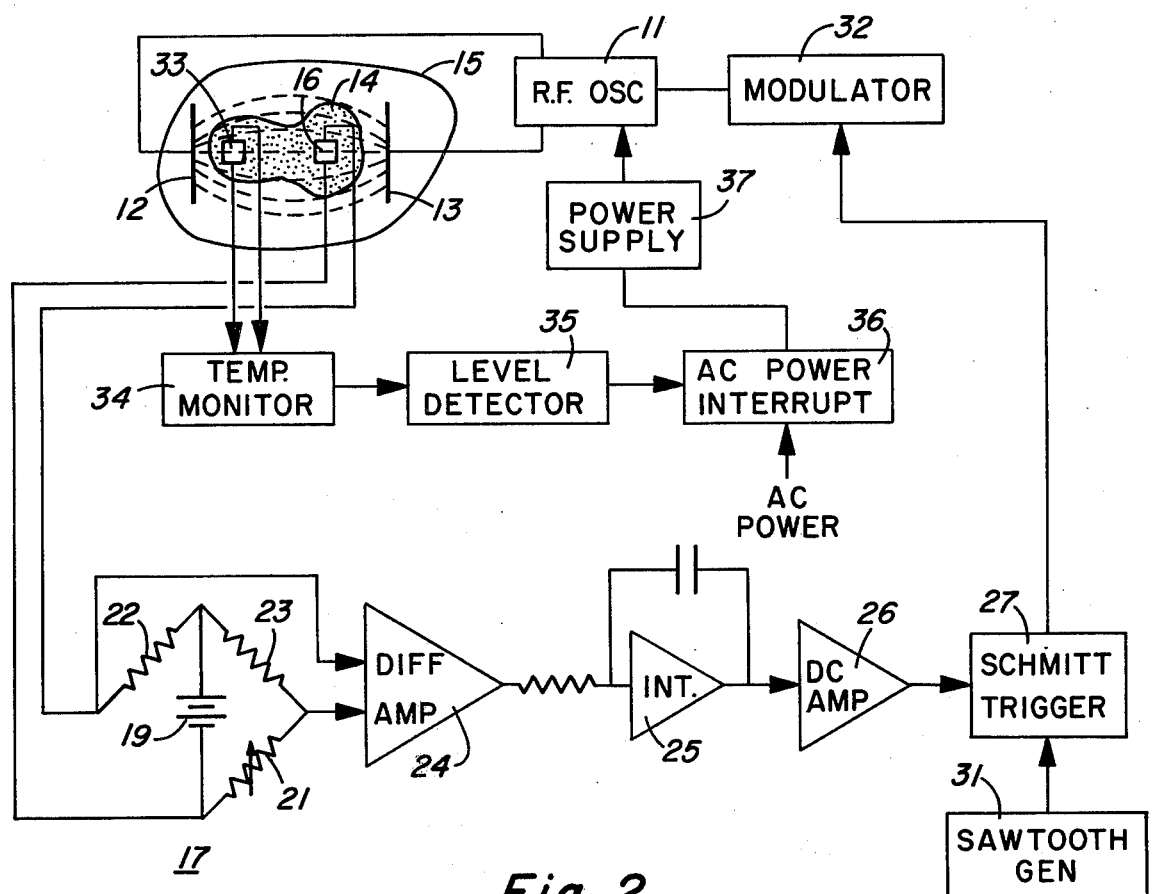
FIG. 2 is a schematic diagram of a circuit employed in connection with the present invention.

Referring now to FIG. 2, generator 11 in the form of an rf oscillator, applies an rf field across electrodes 12 and 13. The field is concentrated in a tumor volume 14 embedded in body tissue indicated by the reference numeral 15. The temperature $T + \Delta T$, desired in the tumor volume 14, is sensed by a thermistor 16 embedded in the tumor volume. Thermistor 16 is connected in a Wheatstone bridge circuit 17, powered by a suitable dc source such as battery 19. The desired temperature is set by a potentiometer 21, the bridge being balanced when thermistor 16 is at preset temperature. Resistors 22 and 23 complete the conventional Wheatstone bridge. Any unbalance of the bridge caused by variation from the preset temperature $T + 66 T$ is sensed by a differential amplifier 24. The bridge unbalance signal from differential amplifier 24 is integrated by integrator 25 and applied to dc amplifier 26 wherein the unbalance voltage is further amplified. The unbalance voltage is applied to one terminal of Schmitt trigger circuit 27. The output of the sawtooth generator 31 is also applied to Schmitt circuit 27. DC operational amplifier 26 normally provides a constant output voltage in the absence of any error in temperature from thermistor 16. Sawtooth generator 21 triggers the Schmitt trigger circuit to normally provide a square-wave output with zero output from dc operational amplifier 26. The relative length of the positive and negative going portions of the square-wave from Schmitt trigger circuit 27 are varied by the + voltage output from dc operational amplifier 26, thus to decrease the output from rf oscillator 11 the positive going portion of square-wave may be reduced as the output voltage from dc amplifier 26 becomes more negative. Contrarily the positive part of the square-wave will increase with respect to the negative portion as the voltage output from dc amplifier 26 becomes positive. The output wave form from Schmitt trigger 27 is applied to a suitable amplitude modulator 32 which varies the duty cycle, the ratio of on-time to off-time, of rf oscillator 11. A switching rate of 100 times per second, determined by the frequency of sawtooth generator 31, may conveniently be employed. A power amplifier, not shown, may be provided to further amplify the output of rf oscillator 11. Normally a maximum of 100 watts of effective power may be required. However, in the case of a small tumor the effective output power may be only 2 watts. A safety device is provided including a temperature sensitive thermistor 33 inserted in the tumor volume adjacent control thermistor 16. Safety thermistor 33 is connected in circuit with temperature monitor 34, which may be substantially identical to Wheatstone bridge 17. The output of the temperature monitor 34 is applied to a level detector 35 which, upon sensing a dangerous temperature level, provides an output signal to ac power interrupt circuit 36, which shuts off ac power to the power supply 37, in turn cutting off rf oscillator 11.

As discussed hereinabove, bone tissue has a substantially higher electrical resistance than muscular tissue or other soft tissues. FIG. 2 illustrates an application of the present invention in connection with tumorous tissue in bone marrow. The arrangement illustrated exploits not only the higher electrical resistance of bone but also the thermal insulating properties thereof. Electrodes 12 and 13 are placed into the bone marrow adjacent to tumorous body 14. The heat field resulting from the insertion of electrodes 12 and 13 into the bone tissue can be extremely well localized in the tumorous tissue 14 since very little current can flow in the bone and also since very little heat can be transferred through the bone into the surrounding muscle tissue.

It will be noted that large blood vessels are not damaged by the heat radiated into tumor tissue adjacent thereto. While the radio frequency current provides similar levels of energy density in the tumor, in the blood vessel wall and in the blood flowing through the vessel, the circulating blood removes heat from the blood vessel wall, resulting in a blood vessel that is cooler than the surrounding tumor and therefore less sensitive to ionizing radiation.

Figure 4:
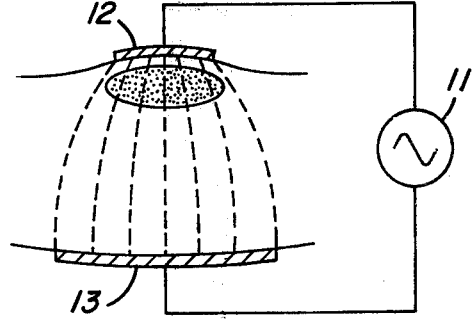
FIG. 4 illustrates the present invention in connection with an internal but superficial tumor.
Figure 5:
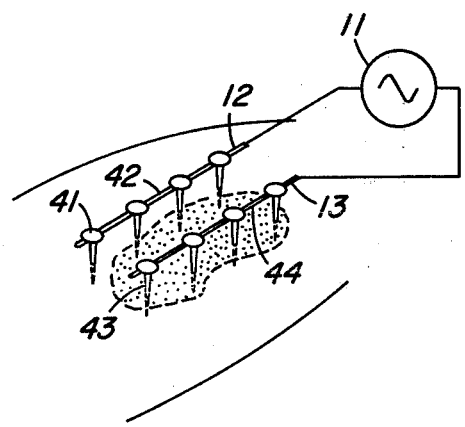
FIG. 5 illustrates an electrode configuration for use with internal tumors.

Superficial tumors may be heated by the electrode configurations illustrated in FIGS. 4 and 5. As illustrated in FIG. 4 a small electrode 12 is placed directly over the tumor volume while larger remote electrode 13 provides a return path to oscillator 11. By employing different relative electrode areas, since the same current flows through each electrode surface, current density is higher adjacent to the smaller electrode 12. Therefore the temperature rise in the region of the smaller electrode 12 is greater. This treatment approach is most useful in those cases where the treatment volume is at least partially convex from the normal body surface and where there is a minimal amount of fat between the electrode surface and the tumor volume.

FIG. 5 illustrates an alternate method for the heating of superficial tumors that requires neither the convex surface nor thin fat layer. In this approach, electrode 12 comprises a row of stainless steel pins such as 41, interconnected by a thin wire braid 42. Electrode 13 comprises a similar row of stainless steel pins 43, interconnected by braided wire 44. The stainless steel pins are inserted on each side of the treatment volume in parallel rows. When the distance between the two parallel rows of pins is small compared to the dimensions on the sides of each plane defined thereby, current density and therefore temperature rise is approximately uniform between the planes defined by the pins. More than two planes may be used when necessary, if the adjacent planes are not connected to the same output line of generator 11. In a modification of a method illustrated in FIG. 5, a thin layer of insulation may be placed on a selected portion of each needle to produce a condition whereby current flow is confined to the portion of the needle plane deeper in the tissue.

Figure 7:
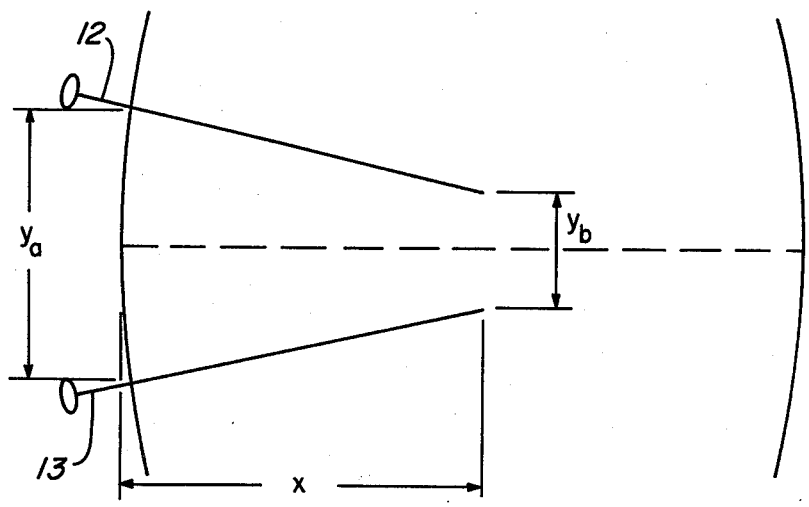
FIG. 7 is a side-view of a configuration of FIG. 6.
Figure 6:
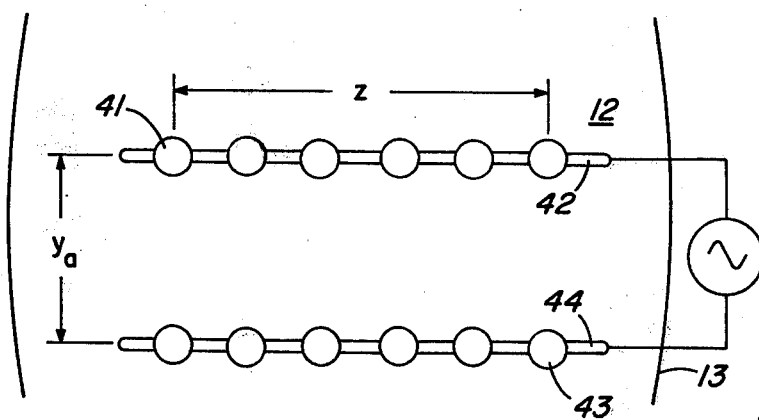
FIG. 6 illustrates a modification of the electrode configuration of FIG. 5.

Referring now to FIGS. 6 and 7, a modification of the approach of FIG. 5 enabling concentration of radio frequency current in deeper tissues is illustrated. Electrodes 12 and 13, comprising needles 41 interconnected by braid 42, and needles 43 interconnected by braid 44, respectively, are inserted into the tissue in a converging manner. The current density is considerably greater in the region deep in the tissue where the needle planes are closer together. Assuming homogenous resistivity in the tissue involved, the current density may be made twice as great where the planes are nearest one another as compared to the surface current density. This results in a temperature rise that is approximately four times as high in the deep treatment volume as on the surface. If there is a significant fat layer at the surface, current density and temperature will be even lower in that area, resulting in even better localization of heat in depth. Exemplarily, the needles 41 may be 1 mm in diameter and placed 5 mm apart for a distance across the surface of 9½ cm indicated as Z in FIG. 6. Distance between the electrode planes may be, exemplarily, 4 cm on the surface and 2 cm at maximum depth, corresponding to the dimensions $Y_a$ and $Y_b$ in FIG. 7. A thermistor inserted 4 cm deep and at right angles to the electric field near the region of highest electric field density measured a temperature of approximately 38.6° C at the surface. At a depth of approximately 6½ cm the measured temperature is approximately 44° C.

Figure 8:
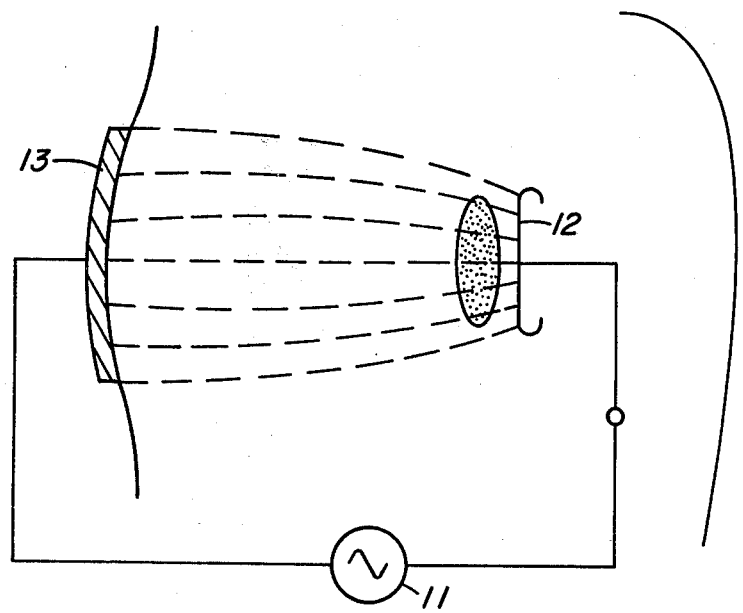
FIG. 8 schematically illustrated the employment of an implanted electrode in connection with a very deep tumor volume.

Deeply embedded tumorous tissue may be subject to rf heating in accordance with the present invention in the manner illustrated in FIG. 8. As discussed hereinabove, rf generator 11 is connected to electrodes 12 and 13. Electrode 12 is a metallic mesh or plate implanted within the patient on one side of the treatment volume. Edges of the mesh or plate may be curved to minimize the possibility of high fields in the area of the edges, where such fields are undesirable. A larger conductor, which may conveniently comprise a fabric soaked in a saline solution, is applied externally at the time treatment is to be made. As disclosed hereinabove in connection with FIG. 4, the current density is higher in the vicinity of a smaller internal electrode, resulting in a greater energy dissipation and temperature rise in that area.

There are many other variations of the present invention possible. Exemplarily, a cylindrical conduction probe may be inserted into the colon or esophagus. The external electrode may then be a saline solution soaked cloth placed around the entire trunk. This results in an approximately coaxial geometry wherein the current density decreases in inverse proportion to the distance from the internal electrode. Temperature rise decreases approximately as the inverse of that distance squared, depending upon the heat transfer parameters of the tissues involved in a given case.

What we claim:

1. A method of treating tumorous tissue in situ comprising heating substantially only the said tumorous tissue by placing at least two electrodes in operative relationship, passing radio frequency current having a frequency less than 1 MHz substantially directly through the tumorous tissue, forming and placing electrodes to shape the field of said radio frequency current by inserting in the patient's body a plurality of electrically conductive pins on either side of tumorous tissue with the distance between opposite pins being inversely proportional to the required radio frequency field intensity and current; electrically interconnecting said pins on one side of said tumorous tissue; electrically interconnecting said pins on the other side of said tumorous tissue; and applying said radio frequency current to said interconnected pins on both sides of said tumorous tissue.

2. In the method set forth in claim 1, inserting said pins on either side of embedded tumorous tissue with the embedded ends closely adjacent to said tumorous tissue and outer ends separated, whereby radio frequency current is concentrated in said tumorous tissue.

* * * * *